United States Patent [19]

Schwalm et al.

[11] Patent Number: 5,220,037
[45] Date of Patent: Jun. 15, 1993

[54] SULFONIUM SALTS AND USE THEREOF

[75] Inventors: Reinhold Schwalm, Wachenheim; Andreas Boettcher, Nussloch, both of Fed. Rep. of Germany

[73] Assignee: BASF Aktiengesellschaft, Ludwigshafen, Fed. Rep. of Germany

[21] Appl. No.: 825,752

[22] Filed: Jan. 27, 1992

Related U.S. Application Data

[63] Continuation-in-part of Ser. No. 551,791, Jul. 12, 1990, abandoned.

[30] Foreign Application Priority Data

Jul. 22, 1989 [DE] Fed. Rep. of Germany ........ 3924299

[51] Int. Cl.$^5$ .................. C07D 333/10; C07C 69/017; C07C 323/10; C07C 323/11
[52] U.S. Cl. .............................. 549/78; 549/79; 549/3; 549/4; 562/30; 560/1; 568/45; 568/49; 568/53; 568/54; 568/51
[58] Field of Search .................. 568/39, 52, 49, 53, 568/45, 51, 13, 18, 56, 54; 549/79, 78, 3, 4; 560/1; 562/30

[56] References Cited

U.S. PATENT DOCUMENTS

| | | | |
|---|---|---|---|
| 2,807,648 | 9/1957 | Pitt | 568/74 |
| 2,833,827 | 5/1958 | Hahn et al. | 568/74 |
| 4,058,400 | 11/1977 | Crivello | 96/86 |
| 4,058,401 | 11/1977 | Crivello | 96/115 |
| 4,101,323 | 7/1978 | Buhr et al. | 96/35 |
| 4,250,247 | 2/1981 | Sander et al. | 430/270 |
| 4,311,782 | 1/1982 | Buhr et al. | 430/270 |
| 4,491,628 | 1/1985 | Ito et al. | 430/176 |
| 4,737,426 | 4/1988 | Roth | 430/17 |
| 4,806,448 | 2/1989 | Roth | 430/270 |

OTHER PUBLICATIONS

Carre et al., D. Liebermann, Comptes Rendus 193, 1932 p. 70.

(List continued on next page.)

Primary Examiner—Marianne M. Cintins
Assistant Examiner—Margaret J. Page
Attorney, Agent, or Firm—Keil & Weinkauf

[57] ABSTRACT

Novel sulfonium salts useful as photoinitiators for cationic polymerization and for producing relief patterns and relief images have the general formula (I)

$$R_{3-x}\overset{\oplus}{S}(R'-O-R'')_x \quad A^{\ominus} \tag{I}$$

where
$A^{\ominus}$ is a non-nucleophilic counterion,
x is 1, 2 or 3,
R is a hydrocarbon radical
R' is arylene or substituted arylene, and
R" is $$\begin{array}{c} R^1 \\ | \\ -C-R^2 \\ | \\ R^3 \end{array}$$

where
$R^1$, $R^2$ and $R^3$ are each alkyl or monohalogenated or polyhalogenated alkyl or $R^1$ and $R^2$ are each hydrogen or alkyl, and $R^3$ is phenyl, alkenyl or cycloalkenyl, or $R^1$ is hydrogen, and $R^2$ and $R^3$ form ethylenically unsaturated ring, or $R^1$ and $R^2$ are each hydrogen, alkyl, cycloalkyl or aryl, and $R^3$ is alkoxy or $R^1$ is hydrogen or alkyl and $R^2$ and $R^3$ are each alkoxy, aryloxy or substituted aryloxy.

5 Claims, No Drawings

OTHER PUBLICATIONS

Synthesis of Carboxylic and Carbonic Ortho Esters, DeWolfe (1974), p. 153.
Chem. Ber. 88, 91 (1955), Schmidt et al.
J. Amer. Soc. 73, 5765 (1967), Geissman et al.
G. H. Wiegand et al., J. of Org. Chem. 2671 (1986).
Crivello, Cationic Polymerization-Adv. in Polym. Sci., 62, pp. 1–47, (1984).
Hiroshi et al., Org. Coatings and App. Polym. Sci., Proc. (48), pp. 60–65, 1983.
Protection for Phenols and Catechlos, Greene et al., Wiley & Sons, pp. 87–111, 1980.
Vasillu et al., Chemical Abstracts, 64, 19466 (1966).
D. Liberman, Comptes Rendus, 187, 1425 (1933).
Buchi et al., The Total Synthesis of Racemic Aflatoxin $B_{12}$, pp. 6745–6753, 1967.
Crivello et al., "Photoinitiated Polymerization by Dialkyl-4-hydroxy phenylsulfonium Salts", J. of Polymer Science, vol. 18, pp. 1021–1034, 1967.

SULFONIUM SALTS AND USE THEREOF

This application is a continuation-in-part of application Ser. No. 07/551,791, filed on Jul. 12, 1990, now abandoned.

The present invention relates to novel sulfonium salts which in addition to the sulfonium group contain certain functional groups and to radiation-sensitive mixtures containing same. These sulfonium salts are suitable for use as photoinitiators for photoinitiated cationic polymerization and for producing relief images and patterns.

Sulfonium salts have long been known in the literature (cf. for example H. M. Pitt, U.S. Pat. No. -A- 2,807,648 (1957); W. Hahn and R. Stroh, U.S. Pat. No. -A-2,833,827 (1958); and G. H. Wiegand and W. E. McEwen, J. Org. Chem. 33 (1968), 2671).

Photoinitiators are almost exclusively sulfonium salts having complex, non-nucleophilic counterions, such as the photoinitiators developed by Crivello for cationic polymerization (cf. for example U.S. Pat. No. -A- 4,058,400 and U.S. Pat. No. -A-4,058,401). The use of onium salts in cationic polymerization has been reviewed by Crivello in Cationic Polymerisation—Iodonium and Sulfonium Salt Photoinitiators, Advances in Polym. Sci. 62 (1984), 1-48.

The use of onium salts in photoresist materials is described for example in Possibilities for Photoimaging Using Onium Salts, Crivello in Corporate Research and Development, General Electric, Schenectady, N.Y. (1983) and by Ito and Willson in Org. Ctgs. and Appl. Polym. Sci. Proc. 48 (1983), 60, and U.S. Pat. No. -A- 4,491,628.

The prior art sulfonium salts are very effective initiators of polymerization and effective acid donors in photoresist materials; however, none of the abovementioned sulfonium salts contains acid-labile groups which are detachable by the action of radiation and dramatically affect the solubility characteristics of the compounds.

DE-A-3,721,740 describes sulfonium salts of the general formula

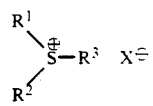

where $R^1$, $R^2$ and $R^3$ are identical or different and each is an aliphatic or aromatic radical which may contain a hetero atom, or two of $R^1$ to $R^3$ combine to form a ring, with the proviso that at least one of $R^1$ to $R^3$ contains at least one acid-cleavable group, it being possible for one of $R^1$ to $R^3$ to be attached to one or more further sulfonium salt residues, optionally via acid-cleavable groups, and $X^\ominus$ is a non-nucleophilic counterion. The acid-cleavable groups mentioned as preferred are tertbutoxycarbonyl and trialkylsilyl groups.

Ethers and acetals/ketals as protective groups for phenols have long been known (cf. for example Protective Groups in Organic Synthesis, Th. W. Greene, ed., John Wiley & Sons, New York (1980), chapter 4: Protection of Phenols and Catechols).

It is an object of the present invention to identify among the phenol-protecting protective groups those which are suitable for sulfonium salts in order thereby to make available photoinitiators of high sensitivity which ideally are effective over a broad range of the electromagnetic wave spectrum and undergo a dramatic change in their solubility characteristics on irradiation.

We have found that this object is achieved in a very advantageous manner by the specific sulfonium salts provided by the present invention.

The present invention accordingly provides sulfonium salts of the general formula (I)

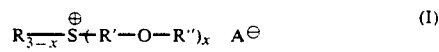

where
$A^\ominus$ is a non-nucleophilic counterion,
x is 1, 2 or 3,
R is alkyl, cycloalkyl, aryl, substituted aryl or, if x=1, a divalent cyclic radical containing $S^\oplus$ as ring member,
R' is arylene or substituted arylene, and
R" is

where
$R^1 R^2$ and $R^3$ are identical or different and each is alkyl of from 1 to 18 carbon atoms or monohalogenated or polyhalogenated alkyl, with the proviso that at least one of $R^1$ to $R^3$ contains a hydrogen atom on the α-carbon, or
$R^1$ and $R^2$ are identical or different and each is hydrogen or alkyl, and $R^3$ is phenyl or substituted phenyl, or
$R^1$ and $R^2$ are identical or different and each is hydrogen or alkyl, and $R^3$ is alkenyl or cycloalkenyl, or
$R^1$ is hydrogen, and $R^2$ and $R^3$ form a preferably five-or six-membered ethylenically unsaturated ring, or
$R^1$ and $R^2$ are identical or different and each is hydrogen, alkyl, cycloalkyl or aryl, and $R^3$ is alkoxy, or $R^3$ combines with $R^2$ via the group $-O-(CH_2)_n$ where n is from 3 to 6 to form a ring, or
$R^1$ is hydrogen or alkyl and $R^2$ and $R^3$ are identical or different and each is alkoxy, aryloxy or substituted aryloxy.

Preference is given to those sulfonium salts according to the present invention where in the general formula (I) R" is tert-alkyl, benzyl, allyl, a ketal radical, an acetal radical or an orthoester radical.

The present invention also provides radiation-sensitive mixtures which contain a sulfonium salt according to the present invention. The present invention further provides a process for photoinitiated cationic polymerization using a sulfonium salt according to the present invention as photoinitiator and processes for producing relief patterns or relief images using in either case at least one sulfonium salt according to the present invention as photoinitiator and solubility inhibitor.

In the general formula (I)

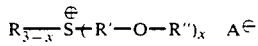 (1)

for the sulfonium salts according to the present invention, the symbols have the following meanings:

$A^{\ominus}$ is a non-nucleophilic counterion, preferably a complex, non-nucleophilic metal halide, such as $BF_4^{\ominus}$, $AsF_6^{\ominus}$ $SbF_6^{\ominus}$ and/or $PF_6^{\ominus}$, or trifluoromethanesulfonate, x is 1, 2 or 3, R is alkyl, for example of from 1 to 6, preferably from 1 to 4, carbon atoms, such as methyl, ethyl or butyl, cycloalkyl, for example of from 5 to 7 carbon atoms, eg. cyclohexyl, aryl, for example phenyl or naphthyl, substituted aryl, eg. t-butylphenyl, or if x=1 a divalent cyclic radical containing $S^{\oplus}$ as ring member, eg. a tetrahydrothiophene ring, R' is arylene, eg. 1,4-phenylene, or substituted arylene, eg. 2-methoxy-1,4-phenylene, and R" is

where $R^1$, $R^2$ and $R^3$ are identical or different and each is alkyl of from 1 to 18, preferably from 1 to 6, carbon atoms or monohalogenated or polyhalogenated alkyl, eg. trifluoromethyl, with the proviso that at least one of $R^1$ to $R^3$ contains a hydrogen atom on the α-carbon, or $R^1$ and $R^2$ are identical or different and are each hydrogen or alkyl, for example of from 1 to 6 carbon atoms, and $R^3$ is phenyl or substituted phenyl, or $R^1$ and $R^2$ are identical or different and each is hydrogen or alkyl, for example of from 1 to 6 carbon atoms, and $R^3$ is alkenyl, for example of from 3 to 6 carbon atoms, eg. allyl or methallyl, or cycloalkenyl, eg. cyclohexenyl, or $R^1$ is hydrogen, and $R^2$ and $R^3$ combine to form a preferably five- or six-membered ethylenically unsaturated ring, eg. cyclohexenyl, or $R^1$ and $R^2$ are identical or different and each is hydrogen, alkyl, for example of from 1 to 6 carbon atoms, cycloalkyl, eg. cyclohexyl, or aryl, eg. phenyl or naphthyl, and $R^3$ is alkoxy, for example of from 1 to 6 carbon atoms, or $R^3$ combines with $R^2$ via the group $-O-(CH_2)_n$ where n is from 3 to 6, preferably n is 4, to form a ring, or $R^1$ is hydrogen or alkyl, for example of from 1 to 6 carbon atoms, and $R^2$ and $R^3$ are identical or different and each is alkoxy, for example of from 1 to 6 carbon atoms, aryloxy, eg. phenoxy, or substituted aryloxy, for example alkylphenoxy.

Examples of substituents for the substituted aryl and arylene radicals are alkyl having from 1 to 6 carbon atoms, such as methy, ethyl, n-propyl, n-butyl, 2-ethylbutyl and n-hexyl; alkoxy having from 1 to 6 carbon atoms, such as methoxy, ethoxy, isopropoxy, n-butoxy and n-pentoxy; and halogen, such as F, Cl and Br. Mixtures of substituents may be present.

Suitable protective groups for the phenolic function of sulfonium salts are preferably according to the present invention those groups which are easily detachable with the aid of acids, for example tert-alkyl groups such as t-butyl or t-amyl, allyl groups such as allyl, cyclohexenyl or alkylcyclohexenyl and benzyl groups such as benzyl, α-methylbenzyl or α,α-dimethylbenzyl and also acetals, such as tetrahydropyranyl groups. Other possibilities include further —C—O—C— compounds which are bonded to the sulfonium salt via the phenolic group, such as orthocarboxylic esters and carboxamidoacetal groups (cf. EP-A-0 022 571 and DE-A-2 610 842), enol ethers and N-acyliminocarbonate groups (see EP-A-0 006 626 and EP-A-0 006 627) and also cyclic acetals or ketals of β-keto-esters or -amides (see EP-A0 202 196).

The remarks that follow concern the synthesis of such sulfonium salts according to the present invention. There are three general ways of alkylating phenols:

a) reaction of the free phenol with diazoalkanes,
b) reaction of alkyl halides with phenol in the presence of a base, and
c) reaction of a phenol with an olefin by acid catalysis.

The best way of preparing the phenolic sulfonium salts in question has been found to be method b), the reaction with alkyl halides. A further possibility for preparing the sulfonium salts in question is the condensation of alkyl phenyl ethers with thionyl chloride to give the corresponding sulfonium salts (cf. for example C. A. 64 (1966), 19466, and D. Libermann, Compt. R. 197 (1933), 1425).

The synthesis of the hydroxyphenylsulfonium salt starting materials is known (cf. J. Polym. Sci., Chem. Ed., 18 (1980), 1021; U.S. Pat. No. -A-2 833 827 (1958) and DE-A3 721 741).

The sulfonium salts can be reacted as described in J. Amer. Chem. Soc. 89 (1967), 6745, J. Amer. Chem. Soc. 73 (1951), 5765, Chem. Ber. 88 (1955), 91, or Tetrahedron Letters 1970, 343, with the corresponding allyl or benzyl halides in the presence of a base under homogeneous or heterogeneous (phase transfer catalysis) reaction conditions to give the correspondingly functionalized sulfonium salts.

The synthesis of those sulfonium salts which contain acetal groups can be carried out similarly to the methods described in Helv. Chim. Acta. 46 (1963), 415, and Synthesis 1974, 153.

Orthocarboxylic ester groups can be introduced into the salts for example by reacting a hydroxyphenylsulfonium salt with diphenoxychloromethane in methylene chloride, tetrahydrofuran or ethyl acetate in the presence of a base, eg. triethylamine (cf. also for example U.S. Pat. No. -A-4 101 323 column 16 lines 40 ff).

The usefulness of the sulfonium salts as photoinitiators for detaching acid-labile side groups in photoresist materials can be demonstrated by spin coating a photoresist solution of poly(t-butyl methacrylate) and 20% by weight, based on the polymer, of a sulfonium salt according to the present invention onto a silicon wafer, subjecting to imagewise exposure, baking and developing. The irradiated areas are completely removable with an alkaline developer, whereas no depletion takes place in the nonirradiated areas. The use of conventional triarylsulfonium salts leaves behind a thin film whose clean removal requires the use of a cosolvent for dissolving the sulfonium salts.

The sulfonium salts according to the present invention are suitable for use as photoinitiators for photoinitiated cationic polymerization of, for example, styrene, alkyl vinyl ethers, cyclic ethers and epoxides.

The sulfonium salts according to the present invention are also very advantageously suitable for use as photoinitiators and solubility inhibitors in the production of photoresist materials, in which case the preferred polymeric binders are phenolic resins, such as novolaks, or poly-p-hydroxystyrene.

In the Examples, the parts and percentages are by weight, unless otherwise stated.

EXAMPLE 1 Synthesis of tris(methylbenzyloxyphenyl)sulfonium hexafluoroarsenate 5 parts of tris(4-hydroxyphenyl)sulfonium hexafluoroarsenate are dissolved in 100 parts of dry tetrahydrofuran while $N_2$ is bubbled through. 3.36 parts of potassium t-butoxide are then added, and the mixture is subsequently stirred for a further 10 minutes. 5.55 parts of α-methylbenzyl bromide are then added dropwise, and the mixture is stirred overnight. The reaction mixture is discharged into 150 parts of ice-water, and the mixture is repeatedly extracted with ethyl acetate. The combined ethyl acetate fractions are dried over a molecular sieve, and the solvent is evaporated off. Recrystallization leaves 4.7 parts (78%) of pure product. IR and H-NMR spectroscopy agree with the expected structure.

EXAMPLES 2 TO 4

Example 1 is repeated, except that the α-methylbenzyl bromide is replaced by the following halides:

| No. | Halide | Yield | Characterization |
|---|---|---|---|
| 2 | Benzyl bromide | 68% | IR, NMR |
| 3 | Cyclohexyl bromide | 82% | IR, NMR |
| 4 | Allyl bromide | 53% | IR |

EXAMPLE 5 Synthesis of tris(t-butyloxyphenyl)sulfonium hexafluorophosphate 2 mol of thionyl chloride and 3 mol of t-butyl phenyl ether are added together in a reaction flask which is cooled with ice-water. Pulverized aluminum chloride is then added a little at a time with stirring until gas evolution ceases. The reaction batch is left to stand overnight and then poured into ice-water. The product separates off as a viscous oil. The oily phase is then washed with diethyl ether to remove unconverted starting material. The crude product obtained is dissolved in methanol and admixed with a stoichiometric amount of silver hexafluorophosphate, dissolved in methanol. Precipitated silver chloride is filtered off, and the solvent is evaporated off. The total yield of the product is 18%. IR and H-NMR spectra confirm the expected structure.

EXAMPLE 6

Example 5 is repeated, except that the silver hexafluorophosphate is replaced by silver hexafluoroarsenate. Yield of characterized product: 21%.

EXAMPLE 7 Synthesis of tris(tetrahydropyranyloxyphenyl)sulfonium hexafluoroarsenate 4 parts of tris(hydroxyphenyl)sulfonium chloride (prepared as described in Carre et Libermann, Comptes rendus 196 (1933), 275) are admixed with 25 parts of dihydropyran and a catalytic amount of hydrochloric acid, and the mixture is stirred at room temperature for 72 hours. The solids are filtered off with suction, repeatedly washed with water and dried. Chromatographic separation gives 2.1 parts of a product of the expected structure. The tetrahydropyranyl-functionalized sulfonium chloride is dissolved in methanol/dimethylformamide, and an equimolar amount of silver arsenate, dissolved in methanol, is added dropwise. Precipitated silver chloride is filtered off, and the solvent is evaporated off in a rotary evaporator. The yield of sulfonium hexafluoroarsenate is 1.8 parts.

EXAMPLE 8 Synthesis of tris(diphenoxymethyloxyphenyl)sulfonium hexafluoroarsenate 20 parts of tris(hydroxyphenyl)sulfonium hexafluoroarsenate are dissolved in 100 parts of tetrahydrofuran. 12.2 parts of triethylamine are added, followed dropwise by the gradual addition of 30 parts of diphenoxychloromethane, and the mixture is stirred at room temperature for 24 hours. The mixture is then washed with water, and the organic solution is dried over a molecular sieve and evaporated in a rotary evaporator. Chromatographic purification leaves 14.8 parts of the expected product. IR and NMR agree with the expected structure.

EXAMPLE 9

A photoresist solution is prepared from 1 part of the sulfonium salt synthesized in Example 6, 3 parts of a poly(p-hydroxystyrene) having a molecular weight of 31,000 g/mol (light scattering) and 7 parts of methylpropylene glycol acetate. The solution is filtered through a filter having a pore diameter of 0.2 μm and applied in a film thickness of about 1 μm to a silicon wafer by spin coating. After baking at 90° C. (1 minute), the photoresist is irradiated with excimer laser light of wavelength 248 nm through a test mask in contact with the wafer surface for 10 seconds. This is followed by a further bake at 90° C. for one minute and development in an alkaline developer of pH 13.0 for 60 seconds. The resist disappears completely in the irradiated areas, while the nonirradiated areas are depleted only by 3%. The result is a resist pattern of high quality.

We claim:

1. A sulfonium salt of the formula (I)

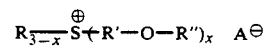

where
$A^\ominus$ is a non-nucleophilic counterion,
x is 3,
R is alkyl, cycloalkyl or aryl,
R' is arylene and
R" is

wherein $R^1$, $R^2$ and $R^3$ are identical or different and each is alkyl of from 1 to 18 carbon atoms or monohalogenated or polyhalogenated alkyl, with the proviso that at least one of $R^1$ to $R^3$ contains a hydrogen atom on the α-carbon.

2. A sulfonium salt of the general formula (I)

$$R_{3-x}\overset{\oplus}{S}(R'-O-R'')_x \quad A^{\ominus} \quad (I)$$

where $A^{\ominus}$ is a non-nucleophilic counterion.

x is 1, 2 or 3,

R is alkyl, cycloalkyl, aryl, substituted aryl wherein the substituents are selected from the group consisting of alkyl of 1 to 6 carbon atoms, alkoxy of 1 to 6 carbon atoms or halogen or, if $x=1$, a tetrahydrothiophene ring, R' is arylene or substituted arylene wherein the substituents are selected from the group consisting of alkyl of 1 to 6 carbon atoms, alkoxy of 1 to 6 carbon atoms and halogen, and R'' is $$\begin{array}{c} R^1 \\ | \\ -C-R^2 \\ | \\ R^3 \end{array}$$

where $R^1$, $R^2$ and $R^3$ are identical or different and each is alkyl of from 1 to 18 carbon atoms or monohalogenated or polyhalogenated alkyl, with the proviso that at least one of $R^1$ to $R^3$ contains a hydrogen atom on the α-carbon, or $R^1$ and $R^2$ are identical or different and each is hydrogen or alkyl, and $R^3$ is phenyl or substituted phenyl wherein the substituents are selected from the group consisting of alkyl of 1 to 6 carbon atoms, alkoxy of 1 to 6 carbon atoms or halogen, or $R^1$ and $R^2$ are identical or different and each is hydrogen or alkyl, and $R^3$ is alkenyl or cycloalkenyl, or $R^1$ is hydrogen, and $R^2$ and $R^3$ form a five- or six-membered ethylenically unsaturated ring, or $R^1$ and $R^2$ are identical or different and each is hydrogen, alkyl, cycloalkyl or aryl, and $R^3$ is alkoxy, or $R^3$ combines with $R^2$ via the group $-O-(CH_2)_n$ where n is from 3 to 6 to from a ring, or an orthoester, or $R^1$ is hydrogen or alkyl and $R^2$ and $R^3$ are identical or different and each is alkoxy, aryloxy or substituted aryloxy wherein the substituents are selected from the group consisting of alkyl of 1 to 6 carbon atoms, alkoxy of 1 to 6 atoms or halogen.

3. A sulfonium salt as claimed in claim 2, wherein in the formula (I) R'' is alkyl or alkoxyalkyl.

4. A sulfonion salt as claimed in claim 2, wherein in the formula (I) R'' is tert-alkyl or benzyl.

5. A sulfonion salt as claimed in claim 2, wherein in the formula (I) R'' is an orthoester radical.

* * * * *

UNITED STATES PATENT AND TRADEMARK OFFICE
CERTIFICATE OF CORRECTION

PATENT NO. : 5,220,037

DATED : June 15, 1993

INVENTOR(S) : SCHWALM et al.

It is certified that error appears in the above-identified patent and that said Letters Patent is hereby corrected as shown below:

IN THE CLAIMS

Claim 2, column 8, line 17, "from" should be --form--.

Signed and Sealed this

Twenty-ninth Day of March, 1994

*Attest:*

BRUCE LEHMAN

*Attesting Officer*   Commissioner of Patents and Trademarks